United States Patent
Cerri et al.

(10) Patent No.: US 6,417,413 B1
(45) Date of Patent: Jul. 9, 2002

(54) PROCESS FOR THE PREPARATION OF HALOGENATED ETHANES

(75) Inventors: Gustavo Cerri; Yuon Chiu, both of Morris County, NJ (US); Biju Z. Perincheril, New Orleans, LA (US)

(73) Assignee: AlliedSignal Inc., Morristown, NJ (US)

( * ) Notice: Subject to any disclaimer, the term of this patent is extended or adjusted under 35 U.S.C. 154(b) by 0 days.

(21) Appl. No.: 09/432,748

(22) Filed: Nov. 3, 1999

(51) Int. Cl.⁷ .................. C07C 17/00; C07C 19/08; B01D 3/34
(52) U.S. Cl. ................ 570/163; 570/164; 570/168; 570/169; 570/172; 203/67
(58) Field of Search .................. 570/163, 164, 570/168, 169, 172; 203/67

(56) References Cited

U.S. PATENT DOCUMENTS

| | | | |
|---|---|---|---|
| 3,258,500 A | 6/1966 | Swamer et al. | 260/653.7 |
| 3,755,477 A | 8/1973 | Firth et al. | 260/653.7 |
| 4,843,181 A | 6/1989 | Gumprecht et al. | 570/169 |
| 4,911,792 A | 3/1990 | Manzer et al. | 203/39 |
| 4,967,023 A | 10/1990 | Carmello et al. | 570/166 |
| 5,087,329 A | 2/1992 | Felix | 203/67 |
| 5,094,773 A | 3/1992 | Manzer et al. | 252/172 |
| 5,155,085 A | 10/1992 | Tung et al. | 502/228 |
| 5,346,595 A | 9/1994 | Clemmer et al. | 203/75 |
| 5,399,549 A | 3/1995 | Felix et al. | 570/169 |
| 5,560,899 A | 10/1996 | Solinas et al. | 423/484 |
| 5,849,160 A | 12/1998 | Homoto et al. | 203/87 |

FOREIGN PATENT DOCUMENTS

| | | |
|---|---|---|
| DE | 0 445 560 | 9/1991 |
| DE | 0 542 290 | 5/1993 |
| WO | WO 95/32168 | 11/1995 |

*Primary Examiner*—Johann Richter
*Assistant Examiner*—Sikarl A. Witherspoon
(74) *Attorney, Agent, or Firm*—Colleen D. Szuch

(57) ABSTRACT

A process for preparing halogenated ethanes, particularly pentafluoroethane, from a mixture produced by the reaction of perchloroethylene, hydrogen fluoride and a recycle stream. The preferred process utilizes phase separation techniques to ensure that less than the azzeotropic amount of HF is included in the product stream, thereby minimizing the hydrogen fluoride that is carried off with the desired products after they are separated from the reaction mixture, and at the same time prevents undesirable byproducts from being recycled to the reaction.

52 Claims, 4 Drawing Sheets

PROCESS FOR THE PREPARATION OF HALOGENATED ETHANES

FIELD OF THE INVENTION

The present invention relates to a process for preparing commercial quality halogenated ethanes, and particularly pentafluoroethane from a mixture produced by the reaction of perchloroethylene and hydrogen fluoride. In particular, this invention provides a process that minimizes the hydrogen fluoride that is carried off with the desired products after they are separated from the reaction mixture, and at the same time reduces the need to recycle undesirable byproducts to the reaction.

BACKGROUND OF THE INVENTION

Pentafluoroethane (herein referred to as R125) is a hydrofluorocarbon (HFC), and chlorotetrafluoroethane (R124) and dichlorotrifluoroethane (R123) are hydrochlorofluorocarbons (HCFCs) that increasingly are being used to replace the environmentally disadvantageous chlorofluorocarbons (CFCs) in refrigeration and other applications. Furthermore, the HFCs and HCFCs are preferably as free as possible of CFCs. Some current regulations call for HFC and HCFC products to contain not more than 0.5 weight percent total CFCs as an impurity, and these regulations may become more restrictive in the future. It is therefore important that commercial HFC and HCFC products have a concentration of CFCs that is as low as possible.

The following table identifies the principal halogenated ethanes and other compounds which will be discussed in this application, and includes their refrigerant (R) numbers, formulas and boiling points at atmospheric pressure, with the compounds listed in boiling-point order. The data is from Stacey, et al., *Advances in Fluorine Chemistry*, pp. 173–175 (1963), except the boiling points for HF and HCl are from *The Merck Index*, Tenth Ed., 1983.

TABLE I

| R-No. | Formula | B.P. (° C.) |
|---|---|---|
|  | HCl | −85.1 |
| 125 | $CHF_2$—$CF_3$ | −48.5 |
| 115 | $CClF_2$—$CF_3$ | −38.7 |
| 124 | $CHClF$—$CF_3$ | −12.0 |
| 124a | $CHF_2$—$CClF_2$ | −10.2 |
| 114 | $CClF_2$—$CClF_2$ | 3.6 |
| 114a | $CCl_2F$—$CF_3$ | 3.0 |
| 133a | $CF_3$—$CH_2Cl$ | 6.1 |
|  | HF | 19.5 |
| 123 | $CHCl_2$—$CF_3$ | 27.1 |
| 123a | $CHClF$—$CClF_2$ | 28.2 |
| 113 | $CClF_2CClF_2$ | 47.6 |
| 1111 | $C_2Cl_3F$ | 71.0 |
| 122 | $CHCl_2$—$CClF_2$ | 71.9 |
| 121 | $CHCl_2$—$CCl_2F$ | 116.6 |
| PCE | $C_2Cl_4$ | 120.8 |

Unless indicated otherwise, hereinafter "R124" shall refer to R124, its isomer R124a, and mixtures of these. Similarly, "R123" refers to R123, its isomer R123a, and mixtures of these, while the term "R114" shall refer to R114, its isomer R114a, and mixtures of these. As can be seen, the difference in boiling points between each pair of isomers is relatively small.

The fluorination of PCE with HF is a well-known process used for the production of various fully and partially halogenated ethanes. See, for example, U.S. Pat. No. 3,755,477, incorporated herein by reference. In this process, the ethylene double bond of the PCE is broken, and hydrogen and fluorine from the HF attach to the two carbon atoms. As the process proceeds, chlorine atoms are successively replaced by fluorine, yielding HCl as a byproduct. At any given time the reactor contains a mix of unreacted PCE and HF, HCl, and various ethanes halogenated with different combinations of chlorine and fluorine atoms, depending on the balance of the different possible fluorination schemes. Various different fluorination progressions may occur simultaneously. For example, and with reference to the list of the halogenated ethanes set forth in Table I, in one fluorination sequence PCE becomes R1111, which successively converts to R121, R122, R123, R124 and finally R125, which is a desired end product. Alternatively, underfluorinated intermediates, including R123 and R123a, can convert to R113, then to R114, and finally R115. This latter reaction scheme is considered undesirable in the production of R125, because R115 is an environmentally undesirable chlorofluorocarbon which is difficult to separate from R125, as discussed below.

After the synthesis reaction, the desired end products generally are separated from the undesired byproducts, intermediates and unconverted starting materials. Conventional methods of separation often include distillation of the reactor product stream followed by water and/or caustic wash to remove acids and then a final drying. The present inventors have come to appreciate that such methods may result in significant losses of HF and may also generate waste streams that must be treated. The HF loss occurs because desired products, such as R125, R124, and R123, form azeotropes with HF. Therefore, with conventional distillation it is impossible to completely remove HF from the desired products. According to such prior processes, the stream or streams which contain the desired HFCs will carry with them slightly more than the azeotropic amounts of HF, thus necessitating further processing of the product stream to remove the HF by, for example, water absorption and/or caustic scrubbing.

Based on the above reaction schemes, the present inventors have appreciated that, in order to promote the production of R125, it is desirable to recycle the underfluorinated intermediates which are most readily fluorinated into R125, such as R121 and R122. Although R123 and R124 may be drawn off as desirable hydrochlorofluorocarbon end products, they may also be recycled to form additional R125. Some or all of the R123 and R124, which may be desirable end products, may also be recycled depending on the desired ratio of final products.

On the other hand, it is undesirable to recycle R114, which tends to fluorinate into R115 rather than R125. R115 is an undesirable CFC which is difficult to separate from R125. As discussed in U.S. Pat. No. 5,346,595, incorporated herein by reference, R125 tends to form an azeotrope with R115, and it is difficult to separate the two compounds in the azeotrope. For this reason, its has heretofore been a practice to allow most or all of the R114 to be carried off in the crude R125. However, this solution was less than satisfactory in the prior processes because it creates another problem. More particularly, R114 has a boiling point that is relatively close to that of HF and greater than the boiling point of R124. According to prior processes, the reactor effluent would first have the HCl removed by distillation and then the HCl-free stream was separated by distillation into a high boiling stream which contained the materials, such as HF, intended for recycle, and a low boiling stream which contained the desired R125. However, in order to ensure that the R114 was included predominantly in the low boiling stream and not in the recycle streams, distillation required, because of the relative volatility of R114 and R124, that substantially all of the R124 was included in the low boiling steam along with the R125. Because of the HF/R124 azeotrope, this stream would carry with it a relatively large amount of HF, which according to prior processes was removed via an undesirable caustic wash or similar operation. Therefore, the prior art solution for preventing recycle of R114 created an increased difficulty and cost in terms of the need to de-acidify additional amounts of HF. As discussed in detail below, the present inventors have discovered a process that is capable of effectively minimizing the amount of R114 recycled to the reaction while at the same time reducing the amount of HF that is contained in the crude product streams.

U.S. Pat. No. 4,843,181 is directed to a method for the production of R123 and R124 by the gas phase reaction of HF with a tetrahaloethylene or with a pentahaloethane over a chromium oxide catalyst. The process of this patent calls for the minimization of R125, and provides no teachings on handling a product stream which is rich in R125.

U.S. Pat. Nos. 4,911,792; 4,944,846; 5,094,773 and 5,560,899 all relate to methods for separating HF from R123 and R124. None of these references provide for such separations in the presence of large amounts of R125.

DESCRIPTION OF THE INVENTION

Figure 1:
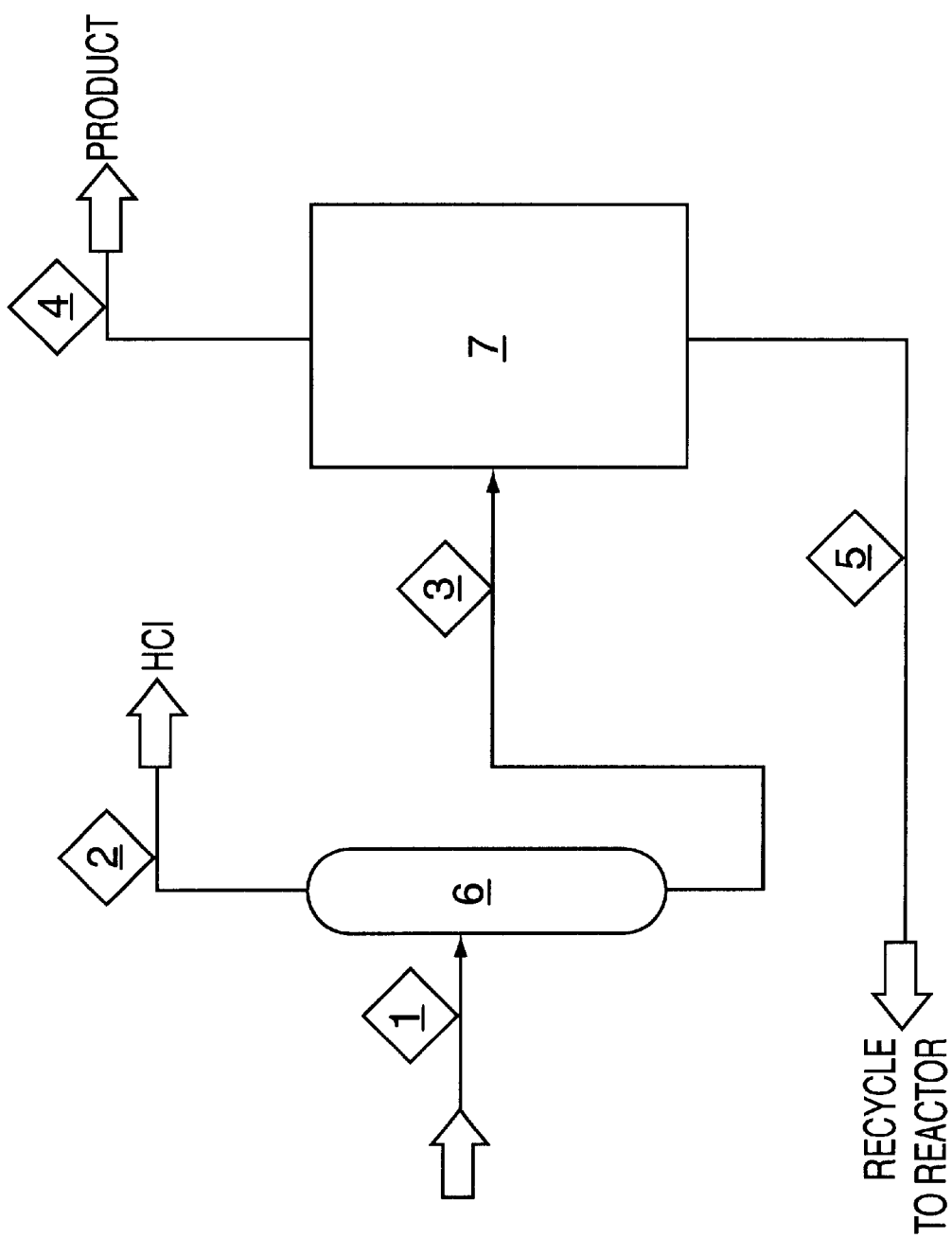
FIG. 1 is a schematic representation of the separation process of the present invention.

The present invention provides a process for the preparation of halogenated ethanes, preferably HFC and HCFC ethanes, and most preferably pentafluoroethane (R125), chlorotetrafluoroethane (R124), and optionally dichlorotrifluoroethane (R123). In general, the present methods comprise:

(a) reacting a chlorinated ethylene, such as perchloroethylene (PCE) with hydrogen fluoride (HF), preferably over a fluorination catalyst, to produce a reactor product stream comprising hydrogen chloride (HCl), HF and one or more halogenated ethanes, preferably including R125;

(b) separating said reactor product stream into an HCl-rich stream and an intermediate product stream;

(c) separating said intermediate product stream into at least a first crude product stream and a recycle stream under conditions effective to ensure that the aggregate amount of HF contained in the total of said crude product stream(s) is less than the aggregate azeotropic amount of HF; and (d) optionally recycling at least a portion of the recycle stream to the reaction of step (a).

All percentages herein are expressed by weight unless indicated otherwise. Furthermore, for purposes of the present application, it will be assumed that the overall process is in steady-state condition when comparing the various process streams.

As the term is used herein, "HCl-rich stream" refers to a stream containing at least 50 weight percent of the HCl present in the reactor product stream.

The term "halogenated ethane" is intended to encompass all fully or partially halogenated ethanes and all mixtures of two or more of these. The present invention is especially well adapted for use in connection with the production of R125, R124, R133a, R123, R122 and R121, as described in Table I above.

For purposes of the present application, the "azeotropic amount" of HF contained in a stream is that amount which would be azeotropically bound to the halogenated ethanes contained in that stream. The "aggregate" azeotropic amount of HF contained in multiple streams is the sum of the azeotropic amounts of HF in all of the streams. The compositions of the HF/HFC azeotropes (in weight percent) that are most important to the present invention are approximately as indicated below:

HF/R125=1.7%/98.3%

HF/R124=6%/94%

HF/R123=17%/83%

As used in the present application, the term "crude product stream" is used to refer to those streams that have sufficiently low concentrations of unwanted components (e.g., HF) and sufficiently high concentrations of the desired halogenated ethane(s) to be considered ready for final processing and/or use or sale as a stream containing the desired halogenated ethane(s). Although the term "crude product stream" is intended to exclude the HCl-rich stream, it will be appreciated by those skilled in the art that the HCl-rich stream is in many embodiments considered to contain valuable product and may also be further refined or processed for use or sale.

An important aspect of the present invention is the use of a separation step in which the aggregate amount of HF in the crude product stream(s) is less than the aggregate azeotropic amount of HF for those streams. As described in more detail hereinafter, the preferred embodiments of the invention utilize a separation step which comprises a phase separation step in combination with one or more distillation steps. The present inventors have discovered that the use of a separation step, such as phase separation, which does not rely on vapor/liquid equilibrium concentration differentials to achieve separation of HF from halogenated ethane(s), preferably including R125, permits a process in which the limitations of the prior art processes can be avoided. Applicants have discovered that phase separation is a particularly preferred separation step for the production of the preferred halogenated ethane(s) of the present invention.

The preferred process of the present invention is shown schematically in FIG. 1. As discussed above, perchloroethylene (PCE) and hydrogen fluoride (HF) are introduced into a reactor (not shown), preferably over a fluorination catalyst, to produce a reactor product stream 1 comprising hydrogen chloride (HCl), HF, R125, and one or more other halogenated ethanes such as R124 and R123. In general, the reactor product stream 1 contains a concentration of unreacted HF greater than the azeotropic amount of HF for that stream. The reactor product stream 1 goes through a first separation process, preferably a distillation separation 6, in which a majority of the hydrogen chloride (HCl) in stream 1 is removed with the HCl-rich stream 2. Preferably, the HCl-rich 2 stream comprises at least about 70 weight percent of the HCl in the reactor product stream, more preferably at least from 90 to about 99 weight percent of the HCl, and most preferably essentially all of the HCl in the reactor product stream. Because the boiling point of the HCl is so much lower than that of the other components, the separation process produces a relatively high boiling mixture of compounds as an intermediate product stream 3 which includes only a minor concentration of HCl and a major proportion of the halogenated ethanes, preferably at least about 75% of the halogenated ethanes in the reactor product stream. The intermediate stream 3 also contains a substantial portion of the HF present in the reactor product stream, preferably at least about 90% of the HF in the reactor product stream, and more preferably substantially all of the HF in the reactor product stream. Thus, the intermediate product stream 3 preferably contains only a residual amount of HCl, and more preferably is essentially free of HCl.

In accordance with an important aspect of the preferred embodiments of the present invention, intermediate product stream 3 is subjected to one or more separation processes represented schematically by separation means 7 whereby the aggregate amount of HF contained in one or more crude product streams 4 is less than the aggregate azeotropic amount of HF for those streams. This is an important aspect of the present invention because prior separation techniques produced crude product streams that undesirably carried at least the azeotropic amount of HF. According to the present invention, separation means 7 preferably includes a phase separator and also preferably operates to produce a recycle stream 5 which contains a major proportion of the HF present in the reactor product stream 1. At least a portion of recycle stream 5 is preferably returned to the reactor for inclusion in the initial reaction. Preferably, the recycle stream contains at least about 98 weight percent of the HF which is in the reactor product stream, and even more preferably at least about 99 weight percent.

In embodiments in which the desired halogenated ethanes comprise R125, R124 and R123, the reactor product stream frequently includes tetrafluorodichloroethane (R114) as one of the other halogenated ethanes. As discussed above, the present inventors have come to appreciate that R114 can fluorinate into pentafluorochloroethane (R115), an undesirable byproduct which is difficult to separate from R125. Therefore, when the reactor product stream comprises R114, as will frequently be the case, the recycle stream preferably contains less than about 10 weight percent (wt. %) of the R114 in the reactor product stream. It is even more preferred that less than about 5 wt. % of the R114 in the reactor product stream be contained in the recycle stream, with less than about 1 wt. % of the R114 being most preferred. The R114 may be included in the R125 crude product stream or, preferably, separated into a different crude product stream.

According to preferred embodiments of the present invention, the reactor product stream 1 comprises a mixture of halogenated ethanes comprising at least about 15 weight percent R125. Furthermore, the present process preferably produces one or more crude product streams 4 which, in the aggregate, contain at least about 90 wt. % of the R125 in the reactor product stream 1, more preferably at least about 95 wt. %, and most preferably at least about 98 wt. %.

In a preferred embodiment, the separation means 7 has only one crude product stream, and this stream contains at least about 90 wt. % of the R125 in the reactor product stream, more preferably at least about 95 wt. %, and most preferably at least about 98 wt. %. Looking at the process from another perspective, it is desired to minimize the amount of R125 included in the recycle stream 5. In accordance with the present invention, preferably less than about 10 wt. % of the R125 in the reactor product stream is recycled to the reactor, more preferably less than about 5 wt. %, and most preferably less than about 1 wt. %.

Figure 2:
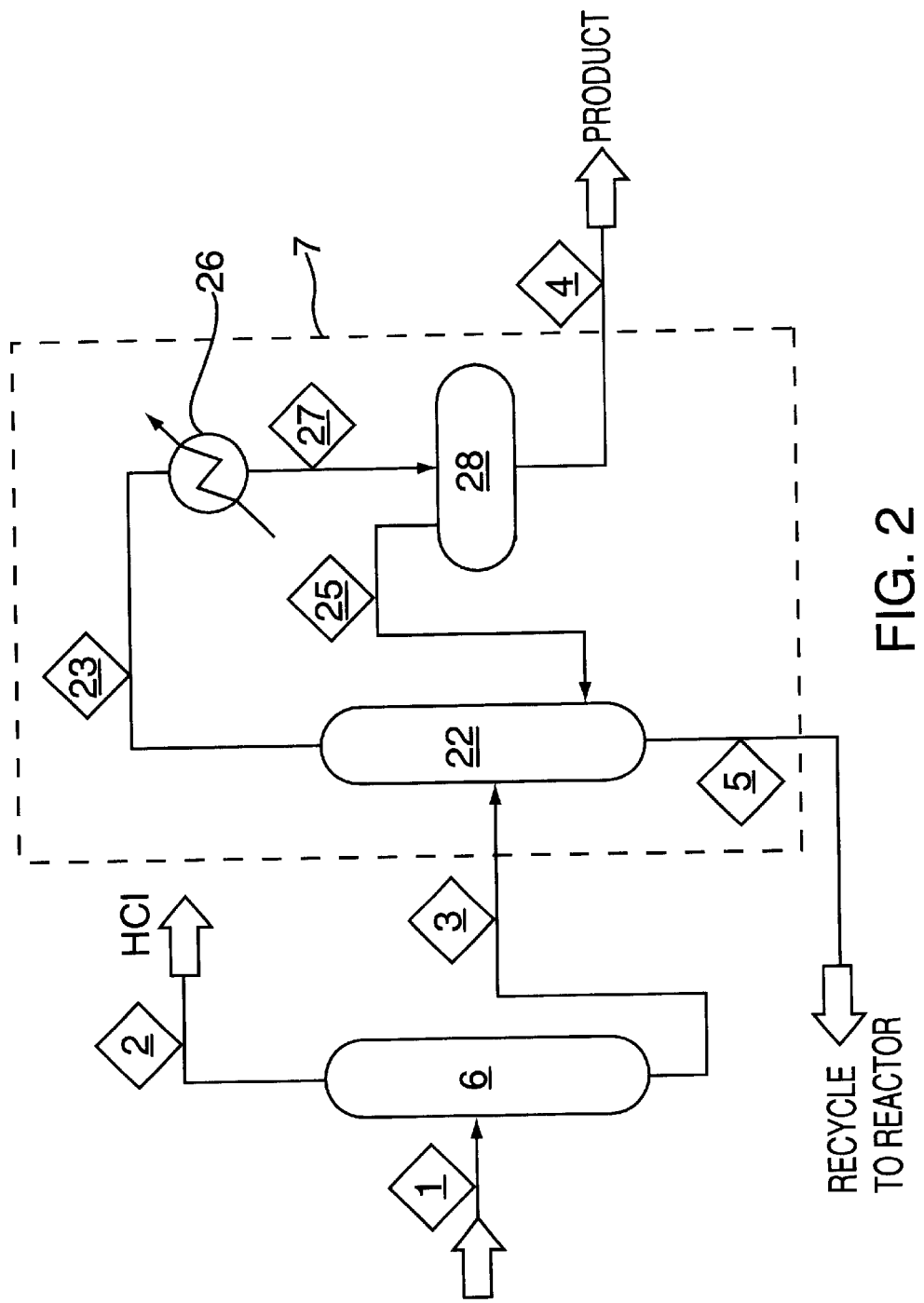
FIG. 2 is a schematic representation of a first embodiment of a separation process in accordance with the present invention.

A preferred embodiment in which separation means 7 has only one crude product stream is illustrated in FIG. 2. This embodiment is particularly suitable for producing a single crude product stream that contains both R124 and R125, and optionally R123, with minimum carry over of HF in the product stream. This embodiment also achieves the desired goal of minimizing the amount of R114 returned to the reactor in the recycle stream. In this embodiment, the reactor product stream 1 is fed to a first distillation column 6 to produce an HCl-rich stream 2 and an intermediate stream 3 that generally has the same characteristics described above in connection with FIG. 1. Stream 3, which is preferably HCl-free and contains most of the halogenated ethanes and unreacted HF, is then fed to a second separator, preferably distillation column 22, where the high boiling reaction intermediates and unconverted starting materials are concentrated in the bottom product to produce recycle stream 5. Preferably the top product stream 23 contains a major proportion of the halogenated ethanes from the reactor stream, and even more preferably essentially all of the R125, R124, R114, and R133*a*. Part or all of any R123 in the distillation feed 3 is also contained in the top product stream 23. Those skilled in the art will appreciate that the particular amount of R123 which is contained in the top product 23 can be varied by manipulation of well known distillation parameters to produce a recycle stream 5 with the desired amount of R123.

According to the embodiment of FIG. 2, top product stream 23 contains significant amounts of HF that in prior processes would be lost in a subsequent de-acidification operation. Applicants have recognized that this feature of the prior art was undesirable for two reasons. First, the HF so lost represents valuable unreacted feedstock that could otherwise be utilized in the reaction. Second, there is a cost and an inefficiency disadvantage associated with such subsequent de-acidification processes. The present process produces desirable crude product streams, that is, streams having less than the azeotropic amount of HF, without the aid of the previously used de-acidification or neutralization processes, such as caustic wash. Put another way, the separation step of the present invention is capable of achieving the above recited low levels of HF in the crude product streams without the need for unit operations that involve the introduction of other materials into the process.

More particularly, the top product stream 23 according to this embodiment is cooled, preferably via heat exchanger 26, to produce a cooled stream 27 having a temperature capable of effecting a liquid/liquid phase separation of a substantial portion of the HF from the remaining components in stream 23. That is, the stream 27 is at a temperature, and preferably at its condensation temperature or below, which produces at least two immiscible liquid phases wherein one of such phases is relatively rich in HF and wherein the other liquid phase contains less than the azeotropic amount of HF, preferably no more than about ⅓ of the azeotropic amount of HF, more preferably no more than about ⅕ of the azeotropic amount of HF, and even more preferably no more than about ⅙ of the azeotropic amount of HF in stream 23. According to preferred embodiments, stream 27 is preferably cooled to a temperature of below about 30° F. (−1° C.), and even more preferably below about 0° F. (−18° C.).

The cooled stream 27 is then introduced into a phase separator vessel, such as decanter 28. The top liquid phase from the decanter, stream 25, contains a major proportion of the HF present in the cooled stream 27 and is preferably recycled to the second distillation column 22. Optionally, part or all of stream 25 can be recycled directly to the reactor. Stream 4 represents the bottom phase from the phase separator, and is an organic-rich phase containing the desired halogenated ethanes and less than the azeotropic amount of HF. If necessary or desired, stream 4 may be further purified by conventional techniques, such as de-acidification to remove any residual acid that may remain. Furthermore, for embodiments in which stream 4 contains a mixture of two or more halogenated ethanes, this stream may be further processed if desired to produce separate streams which are relatively richer than stream 4 in one or more of the halogenated ethanes in the mixture. Furthermore, further processing can be used to remove undesired byproducts (including R114) for disposal. Optionally, part or all of the R123 and/or R124 may be recycled to the reactors for further fluorination to R125 depending on the required product split.

Figure 3:
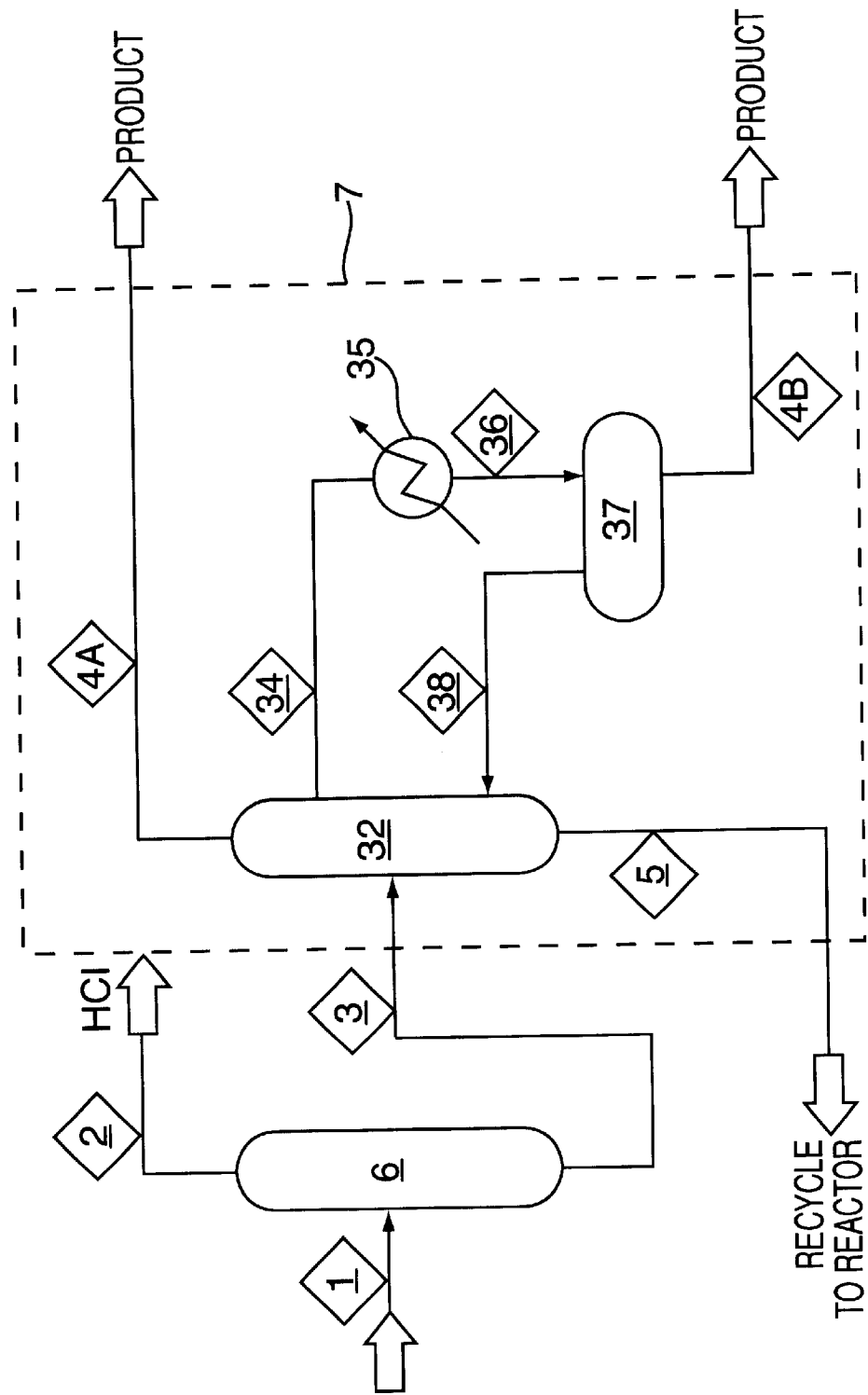
FIG. 3 is a schematic representation of a second embodiment of a separation process in accordance with the present invention.
Figure 4:
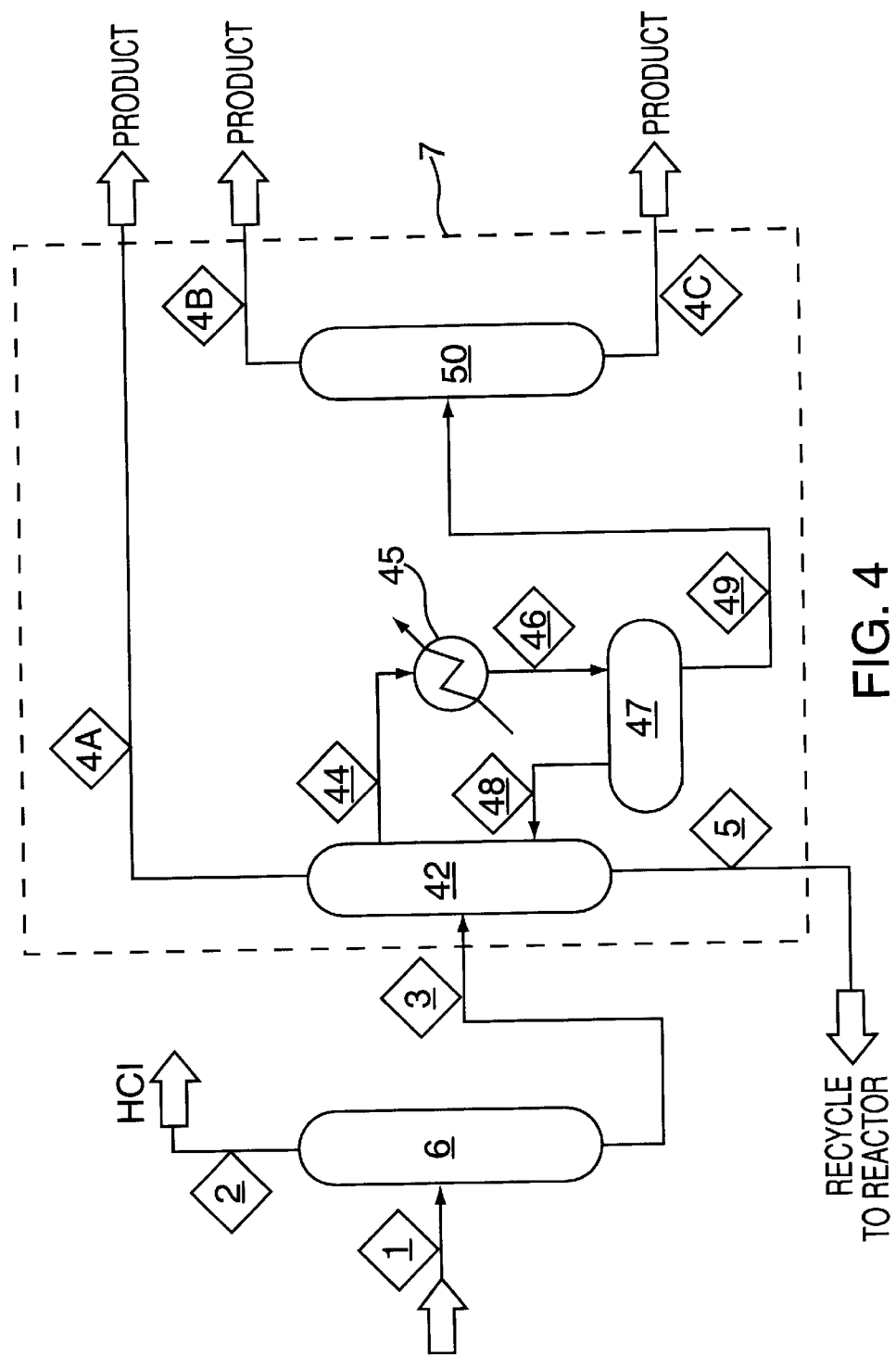
FIG. 4 is a schematic representation of a third embodiment of a separation process in accordance with the present invention.

FIGS. 3 and 4 illustrate two specific embodiments in which more than one crude product is produced. With reference now to the embodiment of FIG. 3, the separator means 7 comprises a series of separation steps which produce a first crude product stream 4A rich in R125 and second crude product stream 4B rich in R124. This embodiment is highly preferred to minimize HF losses to de-acidification while removing R114 from the reactor recycle when no R123 production is desired. In this embodiment, product stream 1 is fed to distillation column 6 to produce an intermediate bottom stream 3, which is essentially HCl-free, and an HCl-rich stream 2. Stream 3, which generally has the characteristics described above in connection with FIG. 1, is then fed to a second distillation 32. In this embodiment, however, distillation column 32 is operated to separate the high boiling-point reaction intermediates, including a major proportion of the HF and R123, and preferably essentially all of the R123, into the bottom recycle stream 5. It is preferred that essentially all the R125 fed to column 32, together with minor amounts of R124 and HF, are removed in the top crude product stream 4A. A side stream 34 is taken from a location intermediate the top and bottom products of the distillation column 32 selected to produce a stream that is rich in R124 and R114. As is explained in more detail below, the side stream preferably contains substantially all of the R124 which is not removed in the overhead stream 4a, and a major proportion, and preferably essentially all, of the R114. The amount of R123 in the side stream 34 is preferably minimized.

The side stream 34 is then cooled in heat exchanger 35 to produce a cooled stream 36 at a temperature capable of effecting phase separation (preferably lower than 30° F. (−1° C.), more preferably lower than 0° F. (−18° C.)). The cooled stream 36 is fed to decanter 37. The top phase from the decanter (stream 38), containing a major proportion of the HF contained in cooled stream 36, is introduced to the second distillation 32 as a feed stream to increase recovery of the organic components that will be in the HF phase and to maximize the amount of HF recovered in the recycle stream 5. Optionally, stream 38 can be recycled directly to the reactor. The bottom crude product 4B from the phase separator 37 is the organic-rich phase having a relatively high concentration of the R124 and a reduced concentration of HF relative to the side stream 34. Optionally, depending on the products which are desired for production, it can be further purified separately from crude product stream 4A or combined with crude product stream 4A and sent to de-acidification.

In an alternative variation of the embodiment illustrated in FIG. 3, stream 4B can be distilled in a third distillation column in which essentially all of the HF and part of the R124 are removed as a top product stream. This top product stream can be recycled directly to the reactor for further conversion to R125 or to distillation column 32. In either case, the HF separated from stream 4B is recycled. The bottoms from the third distillation column, comprising R124, R114, and R133a are essentially acid-free and can be sent directly to final purification.

With reference now to FIG. 4, a further embodiment is described. This embodiment produces crude R123 that is essentially acid-free and can thus avoid wet scrubbing, which can form undesirable byproducts, while removing R114 from the reactor recycle and reducing HF losses. The reactor product stream 1 (containing R125, R124, R123, R114, HCl, PCE, HF, and underfluorinated intermediates and other byproducts of the reaction) is fed to a first distillation column 6 to remove the HCl in the overhead product stream 2. The bottom product stream 3, which generally has the characteristics of stream 3 as described in connection with FIG. 1, is fed to a second distillation 42, where the R125 product and part of the desired R124 product are removed in the top stream 4A. This stream also will contain a small amount of azeotropic HF. The high boiling underfluorinated intermediates (including excess R123 that is not required as product) and unreacted PCE and HF are removed in bottom stream 5 from the second distillation column 42. Lastly, the desired R123 product along with essentially all the R114 byproduct and the rest of RI24, are removed in side stream 44. This stream will also contain significant amounts of HF. The side stream 44 is taken from the second distillation column at a location intermediate between the top and bottom products, and is selected to minimize the amount of R125 as well as components that are higher boiling than R123 in the side stream.

Side stream 44 is then cooled in heat exchanger 45 to produce a cooled stream 46 at a temperature capable of effecting phase separation (preferably lower than 30° F. (−1° C.), more preferably lower than 0° F. (−18° C.)) and fed to a decanter 47. Stream 48 representing the top phase from the decanter, contains a major proportion of the HF contained in cooled stream 46 and is recycled to second distillation 42 at a location below the side stream to improve recovery of the organic components that will be in the HF phase. Optionally, all or a portion of this stream can be recycled to the reactor. The bottom stream 49 from the phase separator is the organic-rich phase and contains a reduced concentration of HF relative to the side stream 44 and a increased concentration of halogenated ethanes, particularly R123 and R124, relative to side stream 44. Stream 49 is sent to a third distillation column 50 to produce a top crude product stream 43 that contains essentially all the R124. Optionally, top crude product stream 4B can be combined with crude product stream 4A to produce a combined crude product stream and sent to de-acidification and final purification. The bottom crude product stream 4C from the third distillation 50 is rich in R123, is preferably essentially acid-free and preferably does not require wet scrubbing, which can result in the formation of undesired byproducts (olefinic impurities, etc.). If necessary or desired, R123 can be purified from stream 4C by distillation techniques known in the art.

As will be appreciated from the above descriptions, certain embodiments of the present invention provide for the separation of R124 from the reactor product stream to produce a crude product stream rich in R124. Preferably at least about 90 wt. %, more preferably at least about 95 wt. %, and most preferably at least about 98 wt. % of the R124 present in the reactor product stream is contained in the crude product streams of such embodiments. In a highly preferred embodiment, at least about 90 wt. % of the R124 from the reactor stream is contained in one crude product stream, more preferably at least about 95 wt. %, and most preferably at least about 98 wt. %. As a further aspect of this embodiment in which one crude product stream contains most of the R124, preferably the R124 in this stream comprises at least about 90 wt. % of the halogenated ethanes in that stream. In other embodiments it may be desirable to recycle some of the R124 to the reactor where it can be further fluorinated into R125.

It will be appreciated that in many embodiments the reaction of PCE with HF produces R123 as a component of the reactor product stream. Some or all of the R123 can be separated into the recycle stream, and sent back to the reactor where it can be further fluorinated into R124 and R125. Optionally, R123 can be separated into one or more of the crude product streams. Applicants have found that it is particularly difficult to remove HF from R123 by aqueous washing techniques. Therefore, in a preferred embodiment of the present invention, as illustrated in FIG. 4, R123 is separated into a crude product stream which preferably contains less than about 0.001 weight percent HF. Because this R123 product is so low in HF, it is not necessary to subject such R123 product to aqueous scrubbing to remove HF.

The crude product streams containing R125, R124 and R123 can be subjected to further purification to remove HF and other impurities in order to produce final products of a more desirable commercial quality. Such purification processes include washing, scrubbing and/or drying, as is well known to those skilled in the art. R125 and R124 both may be purified to remove HF, and any residual HCl, by de-acidification processes which include aqueous washing steps. However, preferably R123 is not subjected to aqueous washing.

The reaction of PCE with HF preferably is carried out in the vapor phase in a reactor at temperatures from about 550° F. to about 750° F., at pressures between atmospheric and about 250 psig, and with a contact time of about 2 to 100 seconds. Preferably, the reaction is carried out over a fluorination catalyst such as, for example, chromium oxyfluoride formed by the partial fluorination of chromium oxide, or other suitable catalysts as are well-known in the art. In the present invention, the reactor product stream contains R125, R124 and R123.

By adjusting various operating parameters it is possible to bias the reactions occurring in the reactor to favor the production of certain halogenated ethane products over others. Such operating parameters include temperature, mole ratio of PCE and HF fed to the reactor, and reaction time, also referred to as contact or residence time. See, for example, Tung, et al., U.S. Pat. No. 5,155,082, which is incorporated herein by reference. In the process of the present invention, R125 is a desired end product. Therefore, the various operating parameters, including temperature, mole ratio and contact time, are preferably adjusted to favor production of R125. In addition, the content of the recycle stream can also be controlled to favor production of R125. By adjusting operating parameters and recycle rates, R125 preferably is made to comprise at least about 15 weight percent of the total of all halogenated ethanes in the reactor product.

The reactor is fed with fresh PCE and HF as needed to maintain the reaction, and a recycle stream which is separated from the reactor product stream is also fed back to the reactor. The process is controlled to ensure that the recycle stream contains as much as possible of the unconverted PCE and HF which exits the reactor.

The reactor product stream is subjected to various separation processes to obtain the desired crude product and recycle streams. As discussed above, the reaction product contains hydrogen chloride as a byproduct of the fluorination process. Because of its relatively low boiling point, the HCl is separated readily by distillation from the other materials in the reactor product. Thus, preferably, the reactor product stream is first separated by distillation to remove the hydrogen chloride prior to further processing, thus producing a stream which has a relatively low concentration of HCl, and which preferably is substantially free of HCl, and which may be referred to herein as the "intermediate product stream" or the "HCl-free stream".

It is contemplated that the HCl-rich stream may also contain some or all of the R125 as well as some of the other halogenated ethanes in the reactor product stream. In such cases, the R125 and other halogenated ethanes are preferably separated from the HCl-rich stream by subsequent separation processes, and are included in one or more crude product streams or the recycle stream.

To help explain the present invention and compare results with other processes, computer simulations were generated using a computer VLLE (Vapor-Liquid-Liquid Equilibrium) model that was developed from laboratory measurements and published data of the vapor-liquid-liquid equilibrium of the components. The Van Laar equation of state was used in the method because it provides a good fit for the data, and reasonably represents the values that would be obtained in actual practice. In each case, the test results are set forth in tables in which the components are listed in order of atmospheric boiling point, as provided in Table I, above. Because these are simulated results calculated relative to a given input, the values of the flowrates can be expressed in any units. For convenience, kilograms per hour (kg/h) are used, unless stated otherwise. Various of the underfluorinated intermediates, including R113, R121, R122 and R1111, are combined into a single entry labeled "Intermediates". As set forth in Table I above, these intermediates generally have relatively high boiling points, above the 27.1° C. boiling point of R123.

Comparative Example 1

In a conventional process, PCE and H are introduced into a reactor under conditions effective to produce a reactor product stream [shown as 1 in FIG. 1] which comprises HCl, HF, R125, R124, R114, R133, R123, PCE and intermediates. The reactor product stream 1 is introduced into conventional distillation column 6 to produce an HCl-rich stream 2 and a bottom product, which is the similar to the intermediate product stream 3 of FIG. 1. The stream is subjected to a second conventional distillation column. In such a process, the bottom product from the first column is relatively HCl-free and is further separated in a second distillation column, with the lower boiling point components removed as a top vapor stream 4 and the higher boiling point components removed as a bottom liquid stream 5. Because of its relatively low boiling point, most of the R125 normally will come out in the top product stream 4. On the other hand, bottom product stream 5 will normally contain most of the higher boiling point components, including the unconverted PCE and HF. According to prior-art processes, the bottom product stream 5 from this distillation contains most of the underfluorinated intermediates (including the R123 and R124 that are not required as product). The bottom product is recycled to the reactor. As discussed above, recycled R123 can fluorinate to R124, and then to R125. How much of the R124 and R123 go to the top or bottom product streams will depend largely on how the distillation process is operated, as is well known to one skilled in the art. Generally, top product stream 4 will contain a large percentage of the desired products (R125, R124, and R123), and a portion of the HF which forms azeotropes with the products and therefore is not removed by the distillation. This top product stream conventionally is treated with water and/or caustic to remove the HF, and is then dried (for example, by treatment with sulfuric acid or over molecular sieve driers).

Table II presents a comparative example illustrating the amount of HF that would be lost to de-acidification in this conventional separation method when part of the R123 is removed from the reaction mixture for recovery as a product.

TABLE II

| STREAM | 1 | 2 | 3 | 4 | 5 |
|---|---|---|---|---|---|
| HCl | 600 | 600 | | | |
| R125 | 300 | trace | 300 | 300 | |
| R115 | 2 | | 2 | 2 | |
| R124 | 500 | | 500 | 500 | |
| R114 | 10 | | 10 | 10 | trace |
| R133a | 10 | | 10 | 9 | 1 |
| HF | 2,400 | | 2,400 | 76 | 2324 |
| R123 | 600 | | 600 | 174 | 426 |
| Intermediates | 100 | | 100 | 9 | 91 |
| PCE | 100 | | 100 | | 100 |
| Total kg/h | 4,622 | 600 | 4,022 | 1,080 | 2,942 |

The crude product stream to de-acidification in Table II is stream 4, while stream 5 is recycled to the reactor for further reaction. As the table shows, about 76 kg/h of HF is contained in stream 4 along with 300 kg/h R125, 500 kg/h R124, 174 kg/h R123, and essentially all the R114 from the reactor product stream. The HF contained in stream 4 is essentially the azeotropic amount plus a small fraction (about 2 kg/h) due to normally expected distillation inefficiency. After de-acidification, the products in stream 4 can be separated by distillation techniques known in the art to produce commercial R125, R124 and R123 products.

Alternatively, in this comparative example, as well as in any of the examples that follow, part or all of the R125, which has a relatively low boiling point, can be separated in the first distillation step with the HCl. In such a process the R125 would then be separated from the HCl in a separate step.

Comparative Example 2

This comparative example illustrates the amount of HF that would be lost to de-acidification in the same conventional separation method used in Comparative Example 1, but when most of the R123 is recycled to the reactor (i.e., essentially no R123 product is recovered). Table III below lists the material balance from such a process.

TABLE III

| STREAM | 1 | 2 | 3 | 4 | 5 |
|---|---|---|---|---|---|
| HCl | 530 | 530 | | | |
| R125 | 300 | trace | 300 | 300 | |
| R115 | 2 | | 2 | 2 | |
| R124 | 500 | | 500 | 500 | |
| R114 | 10 | | 10 | 10 | trace |
| R133a | 10 | | 10 | 9 | 1 |
| HF | 2,400 | | 2,400 | 41 | 2,359 |

TABLE III-continued

| STREAM | 1 | 2 | 3 | 4 | 5 |
|---|---|---|---|---|---|
| R123 | 600 | | 600 | 38 | 562 |
| Intermediates | 100 | | 100 | | 100 |
| PCE | 100 | | 100 | | 100 |
| Total kg/h | 4,552 | 530 | 4,022 | 900 | 3,122 |

Crude product stream 4 is sent to de-acidification and then on to further purification to recover the desired products (R124 and R125). Recycle stream 5 is returned to the reactor for further reaction. As the table shows, about 41 kg/h of HF is contained in stream 4 along with 300 kg/h R125, 500 kg/h R124, and essentially all the R114 from the reactor product stream. The HF contained in stream 4 is essentially the azeotropic amount plus a small fraction (about 2 kg/h) due to normally expected distillation inefficiency.

One disadvantage of this method of separation, whether operated according to Comparative Example 1 or 2, is that the high amount of HF carried in the top product is very undesirable. This HF represents not only a yield loss but also increases the waste water that must be treated from the process. In addition, in order to remove all of the R114 byproduct to keep it from being recycled to the reactor, where it converts to R115, it is also necessary to remove all the R124 with the product stream, even the excess amount that is not required as product. Otherwise, a portion of the R124 could be recycled to the reactor for further fluorination to R125. This excess R124 also increases the amount of azeotropic HF that is lost in the acid removal section, further increasing the size of the acid removal section as well as the final purification section, thereby increasing the cost of the production facility.

Another disadvantage of this method of separation is that tests have shown that small amounts of organic acids and olefinic materials may form in the acid removal/drying section of the process. These materials represent not only a degradation of product into wastes that must be disposed of but some of these impurities are very difficult to separate from R123, increasing the cost of producing specification grade R123 product.

The present invention provides a process which separates the desired R125, R124, and R123 products from the reactor product stream, reduces HF loss, keeps R114 from recycling to the reactor, and avoids having to treat the R123 product with water/caustic wash and drying steps, which have been found to form undesired impurities.

EXAMPLE 1

This example is based on an embodiment of the present invention in accordance with FIG. 4. This embodiment produces crude R123 that is essentially acid-free and can thus avoid wet scrubbing, which can form undesirable byproducts, while removing R114 from the reactor recycle and reducing HF losses.

Table IV lists a material balance for this example, simulating the use of the embodiment shown in FIG. 4 to produce separate product streams of R123 and R124. The column headings in Table IV correspond to the streams identified in FIG. 4. Of additional significance, this example illustrates the reduced amount of HF that would be lost to de-acidification by this embodiment.

TABLE IV

| STREAM | 1 | 2 | 4A | 5 | 44 | 48 | 4B | 4C |
|---|---|---|---|---|---|---|---|---|
| HCl | 600 | 600 | | | | | | |
| R125 | 300 | | 290 | | 11 | 1 | 10 | |
| R115 | 2 | | 2 | | | | | |
| R124 | 500 | | 191 | | 354 | 45 | 309 | |
| R114 | 10 | | 1 | | 10 | 1 | | 9 |
| R133a | 10 | | 1 | 1 | 9 | 1 | | 8 |
| HF | 2,400 | | 17 | 2378 | 63 | 58 | 5 | |
| R123 | 600 | | | | 422 | 186 | 8 | 178 |
| Intermediates | 100 | | | | 89 | 11 | | 11 |
| PCE | 100 | | | | 99 | 1 | | 1 |
| Total kg/h | 4,622 | 600 | 502 | 2,989 | 646 | 113 | 324 | 207 |

This example shows that the combined HF contained in the crude product streams (streams 4A, 4B and 4C) is only about 21 kg/h compared with 76 kg/h of HF in stream 4 of Comparative Example 1. The crude R123 product (stream 4C) contains only trace acidity (that can be easily removed if necessary by adsorption, such as on molecular sieve or alumina), therefore it can be sent directly to product purification. Example 1 and Comparative Example 1 contain approximately equal amounts of crude R125, R124 and R123 and essentially all the R114 from the reactor product in the streams to de-acidification and final purification.

EXAMPLE 2

The embodiment of the invention depicted in FIG. 3 can also be operated to produce R125 and R124 with minimum HF losses to de-acidification while removing R114 from the reactor recycle when no R123 production is required, such that essentially all the R123 is recycled to the reactor.

Table V below lists the material balance from the distillation process depicted in FIG. 3 when operated to produce no R123 product. Since this embodiment essentially does not produce any R123 product, the results may be compared with Comparative Example 2.

TABLE V

| STREAM | 1 | 2 | 4A | 5 | 34 | 38 | 4B |
|---|---|---|---|---|---|---|---|
| HCl | 530 | 530 | | | | | |
| R125 | 300 | trace | 287 | | 13 | | 13 |
| R115 | 2 | | 2 | | | | |
| R124 | 500 | | 14 | | 516 | 30 | 486 |
| R114 | 10 | | | | 10 | | 10 |
| R133a | 10 | | | 4 | 6 | | 6 |
| HF | 2,400 | | 7 | 2385 | 30 | 22 | 8 |
| R123 | 600 | | | | 585 | 15 | 15 |
| Intermediates | 100 | | | | 100 | | |
| PCE | 100 | | | | 100 | | |
| Total kg/h | 4,552 | 530 | 310 | 3174 | 590 | 52 | 538 |

This example shows that the combined HF contained in the crude product streams (streams 4A and 4B) is only about 15 kg/h HF compared with 41 kg/h of HF in stream 4 of Comparative Example 2. This example produces the same amounts of R125 and R124 and removes essentially all the R114 from the reactor recycle as in Comparative Example 2.

As discussed above, it is possible to reduce the HF to de-acidification further if a third distillation column is added to separate the HF together with part of the R124 in stream 37 for recycle to the second distillation column or to the reactor for further reaction to R125. In this case, the HF to de-acidification would be reduced to the 7 kg/h in stream 33.

The crude R124 product (bottom of the third distillation column) would contain only trace acidity (that can be easily removed if necessary by adsorption, such as on a molecular sieve or alumina). Therefore, this product can be sent directly to product purification without de-acidification washing.

EXAMPLE 3

This Example corresponds to the embodiment illustrated in FIG. 2. This embodiment is particularly suitable for producing R124 and R125, and optionally R123 with minimum HF losses to de-acidification while removing R114 from the reactor recycle.

Table VI below lists the material balance for this example, using the distillation process depicted in FIG. 2.

TABLE VI

| STREAM | 1 | 2 | 23 | 5 | 25 | 4 |
|---|---|---|---|---|---|---|
| HCl | 600 | 600 | | | | |
| R125 | 300 | trace | 311 | | 11 | 300 |
| R115 | 2 | | 2 | | | 2 |
| R124 | 500 | | 534 | | 34 | 500 |
| R114 | 10 | | 10 | | | 10 |
| R133a | 10 | | 10 | 1 | 1 | 9 |
| HF | 2,400 | | 77 | 2391 | 68 | 9 |
| R123 | 600 | | 181 | 422 | 3 | 178 |
| Intermediates | 100 | | 10 | 90 | | 10 |
| PCE | 100 | | | 100 | | |
| Total kg/h | 4,622 | 600 | 1,135 | 3,004 | 117 | 1,018 |

This example is operated to produce approximately the same split of R125, R124, and R123 from the second distillation step as in Comparative Example 1. Yet, this example shows that the HF in the crude product stream 4 of this example is only about 9 kg/h HF, as compared with 76 kg/h in stream 4 of Comparative Example 1, as set forth in Table II.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. The foregoing description is by way of example only, and not limiting. The invention is limited only as defined in the following claims and equivalents thereto.

What is claimed is:

1. A process for the preparation of pentafluoroethane (R125), chlorotetrafluoroethane (R124), and optionally dichlorotrifluoroethane (R123) comprising:
   (a) reacting perchloroethylene (PCE) with hydrogen fluoride (HF) over a fluorination catalyst to produce a reactor product stream comprising hydrogen chloride (HCl), HF, R125, R124 and R123;
   (b) separating said reactor product stream into an HCl-rich stream and an intermediate product stream;
   (c) separating said intermediate product stream into at least a first crude product stream and a recycle stream under conditions effective to ensure that the aggregate amount of HF contained in said crude product stream(s) is less than the aggregate azeotropic amount of HF; and
   (d) optionally recycling at least a portion of the recycle stream to the reaction of step (a).

2. The process of claim 1 wherein said separating step(c) comprises separating at least a portion of said HF from said intermediate product stream by phase separation.

3. The process of claim 2 wherein said separating step(c) comprises distilling said intermediate stream into (i) at least a first stream comprising a major proportion of halogenated ethane(s) and a minor proportion of HF and (ii) a second stream comprising a major proportion of HF and a minor proportion of halogenated ethane, followed by separating at least a portion of said HF from said first stream by liquid/liquid phase separation to produce at least one halogenated ethane stream containing less than the azeotropic amount of HF.

4. The process of claim 3 wherein said at least one halogenated ethane stream is said crude product stream.

5. The process of claim 1 wherein said reactor product stream further comprises tetrafluorodichloroethane (R114), and said recycle stream contains less than about 10 weight percent of the R114 in the reactor product stream.

6. The process of claim 1 wherein said recycle stream contains at least about 98 weight percent of the HF in the reactor product stream.

7. The process of claim 1 wherein said crude product stream(s) contain in the aggregate at least about 90 weight percent of the R125 in the reactor product stream.

8. The process of claim 1 wherein said HCl-rich stream contains substantially all of the HCl in the reactor product stream.

9. A process for the preparation of a crude product stream containing pentafluoroethane (R125), chlorotetrafluoroethane (R124) and dichlorotrifluoroethane (R123) comprising:
(a) reacting perchloroethylene (PCE) with hydrogen fluoride (HF) over a fluorination catalyst to produce a reactor product stream comprising hydrogen chloride (HCl), HF, R125, R124 and R123;
(b) separating said reactor product stream into an HCl-rich stream and an intermediate product stream;
(c) separating said intermediate product stream into at least a first crude product stream and a recycle stream, said crude product stream containing (i) at least about 80% by weight of each of the R125 and R124 present in the reactor product stream and (ii) less than the aggregate azeotropic amount of HF for said stream; and
(d) optionally recycling at least a portion of the recycle stream to the reaction of step (a).

10. The process of claim 9 wherein said separating step (c) comprises separating at least a portion of said HF from said intermediate product stream by phase separation.

11. The process of claim 10 wherein said separating step (c) comprises distilling said intermediate stream into said recycle stream and at least a first stream comprising (i) at least about 80% by weight of each of the R125 and R124 and R123 present in the reactor product stream and (ii) not less than the aggregate azeotropic amount of HF for said stream, and separating at least a portion of said HF from said first stream by liquid/liquid phase separation to produce said crude product stream and an HF rich stream.

12. The process of claim 11 wherein at least a portion of said HF rich stream is introduced as a feed stream into said distillation step.

13. The process of claim 11 wherein at least a portion of said HF rich stream is recycled to said reaction step (a).

14. The process of claim 9 wherein said reactor product stream further comprises tetrafluorodichloroethane (R114), and said recycle stream contains less than about 10 weight percent of the R114 in the reactor product stream.

15. The process of claim 9 wherein said recycle stream contains at least about 98 weight percent of the HF in the reactor product stream.

16. The process of claim 9 wherein said crude product stream contains at least about 90 weight percent of the R125 in the reactor product stream.

17. The process of claim 9 wherein said crude product stream comprises less than about 1 weight percent HF.

18. A process for the preparation of a first crude product stream containing pentafluoroethane (R125), and a second crude product stream comprising chlorotetrafluoroethane (R124) comprising:
(a) reacting perchloroethylene (PCE) with hydrogen fluoride (HF) over a fluorination catalyst to produce a reactor product stream comprising hydrogen chloride (HCl), HF, R125 and R124;
(b) separating said reactor product stream into an HCl-rich stream and an intermediate product stream containing at least 90% by weight of the R125 in the reactor product stream;
(c) separating said intermediate product stream into at least said first and second crude product streams and a recycle stream, said first crude product stream containing at least about 80% by weight of the R125 present in the reactor product stream, and said second crude product stream containing (i) at least about 80% by weight of the R124 present in the reactor product stream and (ii) less than the aggregate azeotropic amount of HF for said second crude product stream; and
(d) optionally recycling at least a portion of the recycle stream to the reaction of step (a).

19. The process of claim 18 wherein said separating step(c) comprises separating at least a portion of said HF from said intermediate product stream by phase separation.

20. The process of claim 18 wherein said separating step(c) comprises introducing said intermediate product stream into a distillation vessel, withdrawing said recycle stream as a high boiling mixture from said distillation vessel and withdrawing said first crude product stream as a low boiling mixture from said distillation vessel.

21. The process of claim 20 wherein said separating step(c) further comprises withdrawing from said distillation vessel a side stream comprising (i) at least about 80% by weight of the R124 present in the reactor product stream and (ii) not less than the azeotropic amount of HF for said side stream, and separating at least a portion of said HF from said side stream by liquid/liquid phase separation to produce said second crude product stream and an HF rich stream.

22. The process of claim 21 wherein at least a portion of said HF rich stream is introduced as a feed stream into said distillation vessel.

23. The process of claim 21 wherein HF rich stream is recycled to said reaction step (a).

24. The process of claim 21 wherein said reactor product stream further comprises tetrafluorodichloroethane (R114), and said recycle stream contains less than about 10 weight percent of the R114 in the reactor product stream.

25. The process of claim 21 wherein said recycle stream contains at least about 98 weight percent of the HF in the reactor product stream.

26. The process of claim 21 wherein said first crude product stream contains at least about 90 weight percent of the R125 in the reactor product stream.

27. The process of claim 21 wherein each of said first and second crude product streams comprises less than about 5 weight percent HF.

28. The process of claim 21 further comprising purifying said first crude product streams to produce commercial quality R125.

29. The process of claim 21 further comprising purifying said second crude product stream to produce commercial quality R124.

30. The process of claim 21 wherein said second crude product stream comprises at least about 80 weight percent of the R124 in said reaction product stream.

31. A process for the preparation of a first crude product stream comprising pentafluoroethane (R125), a second crude product stream comprising chlorotetrafluoroethane (R124) and a third crude product stream comprising dichlorotrifluoroethane (R123), the process comprising:

(a) reacting perchloroethylene (PCE) with hydrogen fluoride (HF) over a fluorination catalyst to produce a reactor product stream comprising hydrogen chloride (HCl), HF, R125, R124 and R123;

(b) separating said reactor product stream into an HCl-rich stream and an intermediate product stream;

(c) separating said intermediate product stream into at least said first, second and third crude product streams and a recycle stream, said first crude product stream containing at least about 80% by weight of the R125 present in the reactor product stream, and said second crude product stream containing (i) at least about 50% by weight of the R124 present in the reactor product stream and (ii) less than the azeotropic amount of HF for said second crude product stream, said third crude product stream containing less than the azeotropic amount of HF for said third crude product stream; and (d) optionally recycling at least a portion of the recycle stream to the reaction of step (a).

32. The process of claim 31 wherein said separating step (c) comprises separating at least a portion of said HF from said intermediate product stream by phase separation.

33. The process of claim 31 wherein said separating step (c) comprises introducing said intermediate product stream into a distillation vessel, withdrawing said recycle stream as a high boiling mixture from said distillation vessel and withdrawing said first crude product stream as a low boiling mixture from said distillation vessel.

34. The process of claim 33 wherein said separating step (c) further comprises withdrawing from said distillation vessel a side stream comprising (i) at least about 50% by weight of the R124 present in the reactor product stream and (ii) not less than the azeotropic amount of HF for said side stream, and separating at least a portion of said HF from said side stream by liquid/liquid phase separation to produce a stream rich in halogenated ethanes and an HF rich stream.

35. The process of claim 34 wherein at least a portion of said HF rich stream is introduced as a feed stream into said distillation vessel.

36. The process of claim 34 wherein at least a portion of said HF rich stream is recycled to said reaction step (a).

37. The process of claim 34 wherein said reactor product stream further comprises tetrafluorodichloroethane (R114), and said recycle stream contains less than about 10 weight percent of the R114 in the reactor product stream.

38. The process of claim 34 wherein said recycle stream contains at least about 98 weight percent of the HF in the reactor product stream.

39. The process of claim 34 wherein said first crude product stream contains at least about 90 weight percent of the R125 in the reactor product stream.

40. The process of claim 34 wherein said third crude product stream comprises at least about 80 weight percent R123 and about 0.001 weight percent HF.

41. The process of claim 40 further comprising introducing said halogenated ethane rich stream from said phase separation step to a distillation vessel to produce said second crude product stream and said third crude product stream.

42. The process of claim 34 further comprising purifying said second crude product stream to produce commercial quality R124.

43. The process of claim 34 wherein said second crude product stream comprises at least about 80 weight percent of the R124 in said reaction product stream.

44. The process of claim 34 further comprising purifying the third crude product stream to produce commercial quality R123.

45. The process of claim 34 wherein said third crude product stream comprises at least about 10 weight percent of the R123 in said reaction product stream.

46. A process for the preparation of halogenated ethanes comprising:

(a) reacting perchloroethylene (PCE) with hydrogen fluoride (HF) to produce a reactor product stream comprising R125, R114 and one or more other halogenated ethanes, hydrogen chloride (HCl) and HF;

(b) separating said reactor product stream into an HCl-rich stream and an intermediate product stream containing at least about 90 wt % of the R125 in the reactor product stream;

(c) separating said intermediate product stream into at least a first crude product stream and a recycle stream under conditions effective to ensure: (i) that at least 80 weight percent of the R125 contained in the reactor product stream is present in said at least first crude product stream; (ii) that the aggregate amount of HF contained in said at least one crude product stream is less than the aggregate azeotropic amount of HF for said at least one crude product stream; and (iii) that less than about 10 weight percent of the R114 in the reactor product stream is recycled to the reaction of step (a); and (d) recycling at least a substantial portion of said recycle stream to the reaction of step (a).

47. The process of claim 46 wherein said separating step (c) comprises separating at least a portion of said HF from said intermediate product stream by phase separation.

48. The process of claim 46 wherein said separating step (c) comprises distilling said intermediate stream into (i) at least a first stream comprising a major proportion of halogenated ethane(s) and a minor proportion of HF and (ii) a second stream comprising a major proportion of HF and a minor proportion of halogenated ethane(s), followed by separating at least a portion of said HF from said first stream by liquid/liquid phase separation to produce at least one halogenated ethane stream containing less than the azeotropic amount of HF.

49. The process of claim 48 wherein said at least one halogenated ethane stream is said at least one crude product stream.

50. The process of claim 46 wherein said recycle stream contains at least about 98 weight percent of the HF in the reactor product stream.

51. The process of claim 46 wherein said at least one crude product stream contains in the aggregate at least about 90 weight percent of the R125 in the reactor product stream.

52. The process of claim 46 wherein said HCl-rich stream contains substantially all of the HCl in the reactor product stream.

* * * * *